(12) United States Patent
Osswald et al.

(10) Patent No.: US 11,123,267 B2
(45) Date of Patent: *Sep. 21, 2021

(54) DENTAL RETRACTION COMPOSITION WITH GUANIDINYL-CONTAINING POLYMER

(71) Applicant: 3M INNOVATIVE PROPERTIES COMPANY, St. Paul, MN (US)

(72) Inventors: Peter U. Osswald, Tuerkheim (DE); Henning Hoffmann, Windach (DE); Peter Bissinger, Diessen (DE); Joachim W. Zech, Kaufering (DE); George W. Griesgraber, Eagan, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 64 days.

This patent is subject to a terminal disclaimer.

(21) Appl. No.: 16/346,664

(22) PCT Filed: Nov. 6, 2017

(86) PCT No.: PCT/US2017/060086
§ 371 (c)(1),
(2) Date: May 1, 2019

(87) PCT Pub. No.: WO2018/085744
PCT Pub. Date: May 11, 2018

(65) Prior Publication Data
US 2019/0274929 A1    Sep. 12, 2019

(30) Foreign Application Priority Data
Nov. 7, 2016  (EP) .................................. 16197461

(51) Int. Cl.
*A61K 6/18*    (2020.01)
*A61K 6/69*    (2020.01)
*A61K 6/76*    (2020.01)
*C08L 79/00*   (2006.01)

(52) U.S. Cl.
CPC ............... *A61K 6/18* (2020.01); *A61K 6/69* (2020.01); *A61K 6/76* (2020.01); *C08L 79/00* (2013.01)

(58) Field of Classification Search
CPC ....................................................... A61K 6/18
See application file for complete search history.

(56) References Cited

U.S. PATENT DOCUMENTS

| | | |
|---|---|---|
| 4,522,593 A | 6/1985 | Fischer |
| 5,362,495 A | 11/1994 | Lesage |
| 5,712,027 A | 1/1998 | Ali |
| 5,865,803 A | 2/1999 | Major |
| 5,893,714 A | 4/1999 | Arnold |
| 5,927,562 A | 7/1999 | Hammen |
| 6,383,279 B1 | 5/2002 | Eckhardt |
| 8,563,625 B2 | 10/2013 | Zech |
| 2002/0156149 A1 | 10/2002 | Schaub |
| 2005/0008583 A1 | 1/2005 | White |
| 2005/0287494 A1 | 12/2005 | Yang |
| 2006/0293469 A1 | 12/2006 | Zech |
| 2007/0004858 A1 | 1/2007 | Zech |
| 2008/0220050 A1 | 9/2008 | Chen |
| 2008/0305950 A1 | 12/2008 | Berrada |
| 2010/0255443 A1 | 10/2010 | Dragan |
| 2011/0046262 A1 | 2/2011 | Bublewitz |
| 2011/0151403 A1 | 6/2011 | Pauser |
| 2012/0045400 A1* | 2/2012 | Nowak ................ A61Q 11/00 424/48 |
| 2012/0077142 A1 | 3/2012 | Maurer |
| 2014/0348921 A1 | 11/2014 | Lesage |
| 2014/0377194 A1* | 12/2014 | Strand ................ A61Q 11/00 424/57 |
| 2016/0115430 A1 | 4/2016 | Swanson |
| 2018/0250203 A1* | 9/2018 | Kim ..................... A61K 9/7007 |

FOREIGN PATENT DOCUMENTS

| | | | |
|---|---|---|---|
| JP | 2006056833 | 3/2006 | |
| WO | WO 2006-057535 | 6/2006 | |
| WO | WO 2007-128926 | 11/2007 | |
| WO | WO 2015-157261 | 10/2015 | |
| WO | WO-2015157261 A1 * | 10/2015 | ........... C08G 63/685 |
| WO | WO 2016-196028 | 12/2016 | |

OTHER PUBLICATIONS

Decoteau, Ogledzki, Soroushian, R. D. Perry, Rinse Time of Hemostatic Retraction Pastes, IADR 2011 #1035, https://iadr.abstractarchives.com/abstract/2011sandiego-150036/rinse-time-of-hemostatic-retraction-pastes, 2 pages, Mar. 17, 2011.
Katritzky, "Comprehensive Organic Functional Group Transformation II", Elsevier, 2005, vol. 6, p. 640.
Kim, "Efficacy of Dentifrices Containing Policresulen in Controlling Dental Plaque and Gingivitis", Journal of Korean Academy of Oral Health, 2016, vol. 39, No. 04, pp. 267-272, XP002768317.
Rose, "Bisdiguanides Having Antibacterial Activity", Journal of the Chemical Society, 1956, pp. 4422-4425.
International Search Report for PCT International Application No. PCT/US2017/060086, dated Jan. 5, 2018, 5 pages.

* cited by examiner

Primary Examiner — Michael F Pepitone
(74) Attorney, Agent, or Firm — 3M Innovative Properties Company

(57) ABSTRACT

The invention relates to a dental composition for use as a dental retraction material comprising filler(s), paste forming liquid(s) and guanidinyl-containing polymer(s). The dental composition is typically stored in a capsule with a thin nozzle enabling the delivery of the material in the sulcus of a tooth.

14 Claims, No Drawings

DENTAL RETRACTION COMPOSITION WITH GUANIDINYL-CONTAINING POLYMER

FIELD OF THE INVENTION

The invention relates to a dental composition for use as retraction material for retracting dental tissue from a tooth. The dental composition contains filler(s), paste forming liquid(s) and guanidinyl-containing polymer(s). The dental composition can be stored in a capsule with a thin nozzle enabling the delivery of the material in the sulcus of a tooth.

BACKGROUND ART

For the producing of well-fitting dental crowns and bridges, it is typically necessary to first record the current dental situation in the mouth of a patient.

This can be done by using dental impression materials or by scanning the surface of the dental situation in the mouth of the patient, in particular the surface of the prepared tooth or teeth to be reconstructed.

However, besides the necessity to record the immediate visible surface of the dental situation it is also typically necessary to record the so-called preparation margin of the prepared tooth. The preparation margin is typically close to the gumline and may not be easily visible or recordable.

For better access to the preparation margin often a so-called retraction procedure is suggested where a part of the gingiva is temporarily removed from the hard dental structure. For retracting gingiva from a prepared tooth a cord can be used.

In this respect, a retraction cord is packed between gingival tissue and the margin of the prepared tooth (this region is also often called sulcus) using an appropriate dental instrument. To obtain sufficient vertical and horizontal retraction of gingival tissue, it is often necessary to pack several lengths of retraction cord into the sulcus in order to be able to make a detailed dental impression.

A description of the background in regard to retraction cords can be found e.g. in U.S. Pat. No. 4,522,593 (Fischer).

Generally, dental retraction cords are sometimes difficult to place into the gingival sulcus. The procedure can also be time consuming. It can also be cumbersome to remove the retraction cord prior to taking the impression. Coagulated blood may adhere to the cord and removing it may open the wound again which results in bleeding. For a more convenient placement retraction pastes have been suggested.

A commercially available product to be used for retraction is sold under the name Expasyl™. However, it has been reported that Expasyl™ is only effective under specific, limited conditions when the sulcus is flexible and of sufficient depth. The paste's thickness makes it difficult for some evaluators to express it into the sulcus. Moreover, according to the instruction of use, the viscosity of the composition might change when fluids like water, saliva or blood are absorbed.

Generally, removing non-hardening pastes completely out of the sulcus before taking the impression can be very time consuming and cumbersome. Usually, the paste is rinsed off using water-spray. However, sometimes paste residues are located deep in the sulcus and are thus difficult to remove. These residues might prevent the impression material from flowing into the sulcus area and may negatively influence the setting of the impression material which is subsequently applied. Moreover, after rinsing off the paste with water an additional drying step might be required before the impression can be taken. These removing and drying steps could cause bleeding of the tissue and might make an impression taking step more complicated.

Hardening materials are sometimes easier to remove. However, they are not very hydrophilic. This might cause problems with regard to flowability of the material into the gingival sulcus.

Gingival retraction pastes are known in the dental industry and several pastes are meanwhile available on the market.

U.S. Pat. No. 5,362,495 (Lesage) refers to a method for widening the gingival sulcus without bleeding or oozing, comprising inserting within the gingival sulcus a material in the form of a biocompatible paste which is injectable for external use and having a plastic viscosity measured at 20° C. between about 13,000 and 30.000 Pa*s, wherein said material consisting of a material selected from the group of white clay, seaweed meal and mixtures thereof.

JP 2006/056833 (Yo et al.) relates to a paste consisting of an astringent and filler containing clay mineral, torque, mica, kaolin and/or montmorillonite.

US 2008/0220050 (Chen) relates to a composition for gingival retraction. The pasty composition contains water, clay, glass filler and astringent.

WO 2006/057535 (Kim) describes a composition comprising a certain amounts of kaolin clay, water, aluminium chloride hexahydrate, starch powder, silicone oil and colouring agent.

US 2005/008583 (White) describes a gingival retraction material comprising a carrying medium, a retraction medium and an anti-evaporating component. As an example the following material formula is given: kaolin powder (80 wt. %), aluminium chloride (15 wt. %), water/glycerine sufficient to produce a heavy plastic consistency, flavourings/colour as desired.

US 2005/0287494 (Yang) describes a gingival retraction material prepared by using fibrillated fibres to improve viscosity and combining taste-modifying agent, colour agent and kaolin filler to form a paste-like structure having the viscosity ranging from $31.0*10^6$ cP to $71.0*10^6$ cP.

US 2012/077142 (Maurer et al.) describes a retraction material containing a mixture of layer type 1:1 silicate filler and a layer type 2:1-silicate mineral filler in a ratio 50/50 to 5/95 wt-% as filler. Additional optional ingredients are water, aluminum chloride as astringent as well as silicone oil. In addition the application describes a capsule as application system for delivering the composition into the sulcus.

A dental retraction material having enhanced fluid absorption is disclosed in US 2010/0255443 (Dragen). Such materials are composed of water, aluminum chloride, sodium polyacrylate as absorbing material and fumed silica.

US 2011/046262 (Bublewitz et al.) discloses a pasty insertion for widening the gingival sulcus containing paste-forming agent, a superabsorpber particles and an astringent additive.

US 2014/0348921 (Lesage) describes a retraction paste containing an astringent, preferably aluminum chloride, kaolinitic clay, a texturing agent (carrageenans), water (50-70%), humectant (PEG). These pastes are said to allow for a slower release of aluminium, to be less water-sensitive and to enable a longer treatment time. But as consequence the rinsability of these pastes is significantly reduced.

US 2012/0045400 (Nowak et al.) describes an oral composition comprising a certain polyguanidine compound and an oral acceptable carrier. The oral composition is for preventing or treating periodontal disease and caries and is typically provided as dentifrice.

WO 2015/157261 (Deisenroth et al.) relates to oral care compositions comprising substantive polyesteramides formed from polyols, polycarboxylic acids and arginine. The formed polyesteramides are active in biofilm inhibition, biofilm dissolution and retarding or preventing acid production from oral bacteria. However, all these materials still do not fully address all needs of a practitioner.

Thus, there is still a need for an improved dental composition, which can be used as a dental retraction material.

DESCRIPTION OF THE INVENTION

According to one aspect, there is a desire for a dental retraction composition having a better shelf-life. If possible, the dental retraction composition should also be provided at low packaging costs. Ideally, the dental retraction composition should be easily removable from the sulcus.

It would also be desirable, if the dental retraction composition can easily be delivered through a thin nozzle into the sulcus of a tooth.

One of more of these objects can be addressed by the dental retraction composition described in the present text.

In one embodiment the invention features a dental retraction composition as described in the present text comprising filler(s), paste forming liquid(s), and guanidinyl-containing polymer(s).

In one embodiment the invention features a dental retraction composition as described in the present text comprising phyllosilicate(s), paste forming liquid(s), and guanidinyl-containing polymer(s).

The invention is also related to a kit of parts as described in the present text comprising the dental retraction composition and either of the following components alone or in combination: instruction for use, dental impression material(s), applier(s), and retraction cap(s).

Moreover, described is a method of using the dental retraction composition in a process comprising the step of inserting the composition into the sulcus of one or more teeth.

Another aspect is directed to the use of guanidinyl-containing polymer(s), optionally in combination with policresulen(s) for producing dental retraction composition, preferably for reducing the extrusion force and/or the rinse time of dental retraction compositions.

Unless otherwise specified, within the context of the present text, the following terms have the following meanings.

A "dental composition" is any composition which can be used in the dental or orthodontic field. In this respect the composition should be not detrimental to the patient's health and thus essentially free of hazardous and toxic components being able to migrate out of the composition.

A "dental retraction composition" is a composition enabling the practitioner to retract soft dental tissue (e.g. gingiva) away from hard dental tissue (e.g. tooth) before or during an impression of the tooth structure is made. The dental composition described in the present text is suitable for this purpose.

A "tooth structure" is any tooth structure, prepared or ready for preparation by the dentist. It can be a single tooth or two or more teeth. A tooth structure is also referred to as hard dental tissue in contrast to soft dental tissue (e.g. gingiva).

A "dental impression material" is a material used for making impressions of the tooth structure including the gingiva. A dental impression material is usually applied on a dental impression tray. A dental impression material can be based on different chemical substances and crosslink by various chemical reactions (including addition curing and condensation curing materials). Typical examples include silicone based impression materials (e.g. VPS materials) and polyether based impression materials and mixtures of those.

A "liquid" is any solvent or liquid which is able to at least partially disperse, dissolve or suspend the components being present in the inventive composition at ambient conditions (e.g. 23° C.).

A "paste" is a material that typically consist of a suspension of granular material in a liquid. Pastes can be classified by their viscosity or their consistency comparable to dental impression material (cf. ISO 4823).

A "haemostatic agent" is an agent which is able to reduce bleeding to a certain amount and/or causes blood to coagulate. Haemostatic agents are also sometimes referred to as astringents.

A "particle" means a substance being a solid having a shape which can be geometrically determined. The shape can be regular or irregular. Particles can typically be analysed with respect to e.g. grain size and grain size distribution.

If desired, the particle size can be measured using a Cilas 1064 LD Nass (Cilas, France) light scattering instrument. The Cilas 1064 uses an integrated optical system to cover the range from 0.04 to 500 µm. The mixtures to be analyzed are added to the test chamber filled with water. Ultrasound is applied for about 60 s in order not to alter the particle size distributions and to avoid agglomeration. The raw data is processed with the instrument software using the Fraunhofer approximation, frequently used techniques known to the expert in the art.

"Phyllosilicates" are silicates forming sheets of silicate tetrahedra with $Si_2O_5$. Phyllosilicates can be further divided in sub-groups, e.g. according to the number of sheets or layers arranged with each other.

Within the meaning of the present text, phyllosilicates are divided in the following subgroups: silicate minerals of the 2:1 layer type group and silicate minerals of the 1:1 layer type group.

Clay minerals belong to the group of phyllosilicates can be characterized by the number of layers linked or arranged with each other. This classification is also used in the present text. E.g., in kaolinite, having the ideal formula $Al_2[Si_2O_5(OH)_4]$), two single layers are linked or arranged with each other.

E.g. in muscovite, having the ideal formula $KAl_2(AlSi_3O_{10})(OH)_2$ and belonging to the mica type group of minerals, three layers are linked or arranged with each other.

The terms "crosslinking", "hardening", "setting", "curing" or "curable" are used interchangeable, all referring to the formation of material with a higher molecular weight and/or to the formation of a material having a higher viscosity, by creating a network due to chemical and/or physical interaction.

A composition or solution is "essentially or substantially free of" a certain component, if the composition does not contain said component as an essential feature. Thus, said component is not willfully added to the composition either as such or in combination with other components or ingredient of other components. A composition being essentially free of a certain component usually contains the component in an amount of less than about 1 wt. % or less than about 0.1 wt. % or less than about 0.01 wt. % with respect to the whole composition. Ideally the composition does not contain the said component at all. However, sometimes the presence of a small amount of the said component is not avoidable e.g. due to impurities.

"Ambient conditions" mean the conditions which the inventive solution is usually subjected to during storage and handling. Ambient conditions may, for example, be a pressure of 900 to 1100 mbar, a temperature of 10 to 40° C. and a relative humidity of 10 to 100%. In the laboratory ambient conditions are adjusted to 20 to 25° C. and 1000 to 1025 mbar.

If not indicated otherwise "molecular weight" always means Mw (weight average of the molecular weight) and can be determined for the individual classes of polymers by gel permeation chromatography (GPC) against a standard of defined molecular weight. Suitable measurement methods are known to the person skilled in the art. If not indicated otherwise, wt. % always refers to the weight of the whole composition.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about". The term "comprise" shall include also the terms "consist essentially of" and "consists of".

It has been found that the dental retraction composition described in the present text typically shows a couple of advantageous features.

After application of the dental retraction composition into the sulcus, the composition can be removed or rinsed out within a short period of time.

Moreover, it was found that, if the composition is stored in a specific container with a cannula or nozzle having certain dimensions, the composition can be applied to the sulcus using a commercially available dispensing device with acceptable extrusion forces (e.g. less than or equal to about 150 N).

Further, the use of guanidinyl-containing polymer(s) in the composition enables the formulation of a composition with improved storage stability.

Currently, most dental retraction compositions contain water for dissolving or dispersing other components contained in the composition.

During storage the water may evaporate which typically causes a non-desired increase of the viscosity of the composition.

High viscous compositions typically require a higher force for distributing the composition from a packaging device. In fact, the distribution of a high viscous composition through a thin nozzle into the sulcus of a tooth may become nearly impossible.

To avoid a non-wanted evaporation of water from the composition, the composition has either to be stored under specific conditions (e.g. contained in a sealed pouch) or a reduced shelf-life has to be accepted.

It was found that due to the use of guanidinyl-containing polymer(s), the dental retraction composition described in the present text can be formulated essentially without using or adding water.

The risk of a non-desired increase of the viscosity due to evaporation of a solvent is thus reduced. Thus, a more storage stable composition can be provided.

Further, the composition can be stored in conventional packaging materials without the need for an additional sealed pouch.

In addition, it was found that the flow resistance of the dental retraction composition can be improved, if guanidinyl-containing polymer(s) were used or added.

Finally, due to the astringent properties of the guanidinyl-containing polymer(s), the amount of further, more aggressive astringents like aluminium salts (e.g. aluminium chloride) or other heavy metal salts which are typically used for this purpose can be reduced.

Being able to provide a composition containing a reduced amount or being essentially free of aluminium chloride or other heavy metal salts as astringents, can be beneficial as this may contribute to a better compatibility of the dental retraction material with dental impression materials, in particular with respect to the setting reaction of the dental impression materials.

The dental retraction composition described in the present text is a paste, formed by dispersing filler(s) and/or guanidinyl-containing polymer(s) in paste forming liquid(s).

If desired, the dental retraction composition can be characterized by one or more of the following features alone or in combination:

a) pH: from 5 to 10, if determined with wet pH sensitive paper;

b) Extrusion force: less than or equal to 150 N or below 140 N or below 130 N, e.g. if the dental retraction composition is dispensed from a container having a cannula with the dimension shown in FIG. 4 using a piston as shown in FIGS. 5 and 6 of WO 2010/138433:

c) Rinsing time: less than or equal to 11 or less than or equal to 10 s;

d) Residual gap: more than or equal to 4 or more than or equal 4.5 mm;

e) Flow resistance: more than or equal to 8N or more than or equal to 10N.

In certain embodiments, the combination of the following features is sometimes desirable: a), b) and c). If desired, the features can be determined as outlined in the example section.

As there is no need to add astringents like aluminium chloride, the pH value can be in a range from 5 to 10 or 7 to 9. The composition typically has a sufficient flow resistance (e.g. at least 8 or 10N).

A dental retraction paste, which does not have a sufficient flow resistance, is often difficult to apply into the sulcus. The tooth surrounding tissue forming the sulcus and having certain elasticity often repels the applied composition. That is, if the flow resistance is too low, the paste might be partly squeezed out of the sulcus which may result in an inefficient retraction. By applying and/or packing the dental retraction composition e.g. with the aid of a nozzle or cannula, into the sulcus, a sufficient mechanical retraction of the gingiva can be achieved. The dental retraction composition described in the present text comprises filler(s).

A wide variety of inorganic, hydrophilic or hydrophobic fillers may be employed such as silicates, silica (including quartz and cristobalite), alumina, magnesia, titania, inorganic salts, metallic oxides and glasses.

Other suitable filler(s) include plastic powder, micro- and nanocrystalline cellulose and starch.

The sizes and surface areas of the filler particles can be adjusted to control the viscosity and thixotropicity of the resulting compositions. Some or all of the fillers may be superficially treated with one or more silanating agents, as known to those of ordinary skill in the art. Such silanating may be accomplished through use of known halogenated silanes or alkoxysilanes or silazanes. A combination of reinforcing and non-reinforcing fillers can be preferred.

In this respect, the quantity of reinforcing fillers can range from 1 to 10 wt.-%, in particular from 2 to 5 wt.-% with respect to the whole composition. Typical reinforcing fillers include fumed silica, and the like.

Pyrogenically-prepared highly-disperse silicic acids which have preferably been hydrophobized by surface treatment are preferred as reinforcing fillers. The surface treatment can be carried out, for example with dimethyldichlorosilane, hexamethyldisilazane, tetramethylcyclotetrasiloxane or polymethylsiloxane.

Typical non-reinforcing fillers are phyllosilicates, quartz, cristobalite, precipitated silicas, diatomaceous earth, aluminas, magnesias, titanium dioxide, zirconium silicate, metallic oxides, barium sulphate, calcium carbonate, plaster, glass and the like.

The non-reinforcing fillers can be surface treated, e.g. silanated, or non-surface treated.

Typical average particle sizes are from 2 to 10 μm.

The filler(s) is typically present in the following amounts:
Lower limit: at least 5 or at least 10 or at least 15 wt. %;
Upper limit: utmost 70 or utmost 60 or utmost 55 wt. %;
Range: from 5 to 70 or from 10 to 65 or from 15 to 55 wt. %;
wt. % with respect to the total amount of the dental retraction composition.

The use of phyllosilicates as filler(s) is sometimes preferred.

The nature and structure of the phyllosilicate(s) is not particularly limited unless the desired result cannot be achieved.

Phyllosilicates which can be used include layer type 1:1 silicate minerals, layer type 1:2 silicate minerals and mixtures of layer type 1:1 silicate minerals and layer type 1:2 silicate minerals.

Phyllosilicates from the layer type 1:1 silicate mineral which can be used include kaolinite, lizardite, halloysite and mixtures or combinations thereof, wherein kaolinite is sometimes preferred.

The particle size of the layer type 1:1 silicate mineral is not particularly limited, unless the resulting paste gets to inhomogeneous.

The mean particle size is typically in a range between 0.01 and 100 μm or between 0.1 and 50 μm or between 1 and 25 μm.

The content of the layer type 1:1 silicate mineral in the composition is not particularly limited, unless the desired advantages cannot be obtained.

If present, the layer type 1:1 silicate mineral is typically present in an amount from 1 wt. % to 65 wt. % or from 2 wt. % to 60 wt. % with respect to the whole composition.

Phyllosilicates from the layer type 2:1 silicate minerals which are can be used include mica minerals, talc-pyrophyllite minerals, smectite minerals, vermiculite minerals, illites minerals.

Specific examples include talc, willemseite, pyrophyllite, stevensite, saponite (from the talc-pyrophyllite type group of minerals), stevensite, sponite, sauconite, hectorite, montmorillonite, beidellite, nontronite, volkonskite (from the smectite type group of minerals), phlogopite, biotite, lepidolite, muscovite, illite, glauconite, celadonite (from the mica type group of minerals).

Layer type 2:1 silicate minerals which do not significantly swell when combined with water or show essentially no swelling at all, were found to be especially beneficial. Those silicate minerals include muscovite and phlogopite. For example, the silicate mineral bentonite was found to be not particularly useful as it shows certain undesirable water solubility.

The particle size of the layer type 2:1 silicate mineral is not particularly limited, unless the resulting composition gets too inhomogeneous.

The mean particle size is typically between 0.01 and 100 μm or between 0.1 and 50 μm or between 1 and 25 μm.

If present, the content of the layer type 2:1 silicate mineral in the composition is not particularly limited, unless the desired advantages cannot be obtained.

If present, the layer type 2:1 silicate mineral is typically present in an amount from 20 wt. % to 65 wt. % or from 30 wt. % to 60 wt. % with respect to the whole composition If present, the phyllosilicate(s) are typically present in the following amounts:
Lower limit: at least 20 or at least 25;
Upper limit: utmost 70 or utmost 65;
Range: from 20 to 70 or from 25 to 65;
wt. % with respect to the total amount of the dental retraction composition.

The dental retraction composition described in the present text comprises paste forming liquid(s).

The nature and structure of paste forming liquid(s) is not particularly limited, either unless the desired result cannot be achieved.

Paste forming liquid(s) suitable for preparing the dental retraction composition of the present text include those, which are able to form a paste with the other components present in the composition.

The paste forming liquid(s) can typically be characterized by one or more of the following features alone or in combination:
Molecular weight: utmost 10,000 g/mol;
Boiling point: above 100° C.;
Viscosity: up to 35 Pa*s at 23° C.

A molecular weight in the above range can be beneficial because the risk of an undesired evaporation of the paste forming liquid(s) from the dental retraction composition can be reduced.

A viscosity in the above range can be beneficial because it allows an easy production of the desired paste.

According to one embodiment, the paste forming liquid(s) is a polar liquid.

Specific examples for paste forming liquid(s) include mono-alcohols, glycols (including ethylene glycol, propylene glycol) and the respective alkyl ethers, block-copolymers of ethylene glycol and propylene glycol (commercially available e.g, as Synperonic® and Pluronic®), copolymers of ethylene glycol, propylene glycol and/or tetrahydrofuran, and alkoxylated glycerine or pentaerythritol or other multifunctional alcohols.

In particular, the following paste forming liquid(s) were found to be useful: polyethylene glycol, polypropylene glycol and mixtures thereof.

The amount of paste forming liquid in the dental retraction composition is not particularly limited, unless the desired advantages cannot be obtained.

If the amount of paste forming liquid in the composition is too low, the viscosity of the composition typically increases having the result that the extrusion force needed for dispensing the composition from a container might increase as well.

If the amount of paste forming liquid in the composition is too high, the viscosity of the composition typically decreases having the result that the flow resistance might be insufficient and may hamper the application of the composition into the sulcus.

The paste forming liquid(s) are typically present in the following amounts:
Lower limit: at least 10 or at least 15 or at least 20 wt. %;
Upper limit: utmost 60 or utmost 50 or utmost 40 wt. %;
Range: from 10 to 60 or from 15 to 50 or from 20 to 40 wt. %
wt. % with respect to the total amount of the dental retraction composition.

The dental retraction composition described in the present text comprises a guanidinyl-containing polymer.

It was found that the use of a guanidinyl-containing polymer enables the practitioner the formulation of dental retraction compositions with either a reduced amount or even without the need for an additional astringent such as aluminium chloride.

Alternatively or in addition, the formulation of dental retraction compositions being essentially free of added water is now possible.

Further, the use of a guanidinyl-containing polymer may help to reduce the extrusion force and/or flow resistance of a dental retraction composition.

The term "guanidinyl-containing polymer" includes also polymers where the guanidinyl moiety is present in its protonated form including the salts thereof (in particular chloride and sulphate salts).

Suitable polymers include polyvinylamine, poly(N-methylvinylamine), polyallylamine, polyallylmethylamine, polydiallylamine, poly(4-aminomethylstyrene), poly(4-aminostyrene), poly(acrylamide-co-methylaminopropylacrylamide), poly(acrylamide-co-aminoethylmethacrylate), polyethylenimine, polypropylenimine, polylysine, polyaminoamides, polydimethylamine-epichlorohydrin-ethylenediamine, polyaminosiloxanes, dendrimers formed from polyamidoamine and polypropylenimine, biopolymers, polyacrylamide homo- or copolymers, amino-containing polyacrylate homo- or copolymers, For some embodiments, the preferred amino-containing polymers include polyaminoamides, polyethyleneimine, polyvinylamine, polyallylamine, polydiallylamine and acrylamide based polymers.

As used herein, the term "guanidinyl" refers to a group of the following formula

—NR³—C(=NR⁴)—NR⁴R⁵.

If the guanidinyl group is part of a pendant group, the group $R^3$ refers to hydrogen, $C_1$-$C_{12}$ (hetero)alkyl, or $C_5$-$C_{12}$ (hetero)aryl.

If the guanidinyl group is part of the backbone of the polymer, the group $R^3$ can refer to a residue of a polymer chain.

Each group $R^4$ is independently hydrogen, $C_1$-$C_{12}$ (hetero)alkyl, or $C_5$-$C_{12}$ (hetero)aryl. Group $R^5$ is hydrogen. $C_1$-$C_{12}$ (hetero)alkyl, $C_5$-$C_{12}$ (hetero)aryl, or a group of formula —N($R^4$)₂.

The guanidinyl group can be part of a biguanidinyl group that is of formula —NR³—C(=NR⁴)—NR⁴—C(=NR⁴)—NR⁴R⁵ where the groups $R^3$, $R^4$, and $R^5$ are the same as defined above.

Although any guanidinyl-containing polymer can be used in the cationic form, this polymer is often of Formula (I).

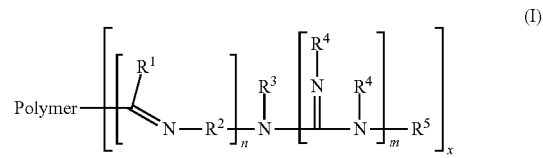

In Formula (I), the group $R^1$ is hydrogen, $C_1$-$C_{12}$ (hetero)alkyl, or $C_5$-$C_{12}$ (hetero)aryl, or a residue of the polymer chain. The group $R^2$ is a covalent bond, a $C_2$-$C_{12}$ (hetero)alkylene, or a $C_5$-$C_{12}$ (hetero)arylene. The group $R^3$ is H, $C_1$-$C_{12}$ (hetero)alkyl, or $C_5$-$C_{12}$ (hetero)aryl, or can be a residue of the polymer chain when n is 0. Each group $R^4$ is independently hydrogen, $C_1$-$C_{12}$ (hetero)alkyl, or $C_5$-$C_{12}$ (hetero)aryl. The group $R^5$ is hydrogen, $C_1$-$C_{12}$ (hetero)alkyl, $C_5$-$C_{12}$ (hetero)aryl, or —N($R^4$)₂. The variable n is equal to 0 or 1 depending on the precursor polymer used to form the guanidinyl-containing polymer. The variable m is equal to 1 or 2 depending on whether the cationic group is a guanidinyl or biguanidinyl group. The term "Polymer" in Formula (I) refers to all portions of the guanidinyl-containing polymer except the x groups of formula —[C($R^1$)=N—$R^2$—]$_n$ N($R^3$)—[C(=NR⁴)—NR⁴R⁵—]$_m$. The term x is a variable equal to at least 1.

Most guanidinyl-containing polymers have more than one guanidinyl group. The number of guanidinyl groups can be varied depending the method used to prepare the guanidinyl-containing polymer. For example, the number of guanidinyl groups can depend on the choice of precursor polymer selected for reacting with a suitable guanylating agent. In some embodiments, the variable x can be up to 1000, up to 500, up to 100, up to 80, up to 60, up to 40, up to 20, or up to 10.

The guanidinyl-containing polymer, in particular the one of Formula (I) is often the reaction product of (a) a precursor polymer and (b) a suitable guanylating agent.

The precursor polymer is often an amino-containing polymer or a carbonyl-containing polymer. When the precursor polymer is an amino-containing polymer, the variable n in Formula (I) is typically equal to 0. When the precursor polymer is a carbonyl-containing polymer, the variable n is equal to 1. If the guanylating agent contains a guanidinyl group or a precursor of a guanidinyl group, the variable m in Formula (I) is equal to 1. If the guanylating agent contains a biguanidinyl group or a precursor of a biguanidinyl group, the variable m in Formula (I) is equal to 2.

In embodiments where n is 0, the base polymer of the guanidinyl-containing polymer is often prepared by reaction of a suitable guanylating agent and an amino-containing polymer. In other embodiments, where n is 1, the guanidinyl-containing polymer is often prepared by reaction of a suitable guanylating agent and a carbonyl-containing polymer.

In those embodiments where n is 0 and the precursor polymer is an amino-containing polymer, the structure of the guanidinyl-containing polymer of Formula (I) can also be written more simply as the structure of Formula (II).

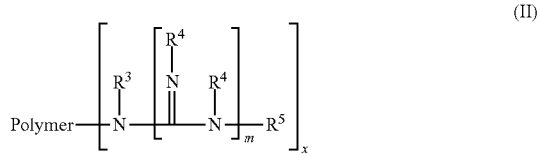

In Formula (II), the group $R^3$ is hydrogen, $C_1$-$C_{12}$ (hetero)alkyl, or $C_5$-$C_{12}$ (hetero)aryl, or can be a residue of the polymer chain. When the guanidinyl group is part of a pendant group. $R^3$ is hydrogen, $C_1$-$C_{12}$ (hetero)alkyl, or $C_5$-$C_{12}$ (hetero)aryl. Each $R^4$ is independently hydrogen, $C_1$-$C_{12}$ (hetero)alkyl, or $C_5$-$C_{12}$ (hetero)aryl. The group $R^5$ is hydrogen, $C_1$-$C_{12}$ (hetero)alkyl, or $C_5$-$C_{12}$ (hetero)aryl, or —$N(R^4)_2$. The variable m is equal to 1 or 2. The term "Polymer" in Formula (II) refers to all portions of the guanidinyl-containing polymer except the x groups of formula —$N(R^3)$—$[C(=NR^4)$—$NR^4R^5$-$]_m$. The term x is a variable equal to at least 1.

The amino-containing polymer used as a precursor polymer to prepare a guanidinyl-containing polymer of Formula (II) can be represented by the formula Polymer —$N(R^3)H$. As noted above, however, the amino-containing polymer typically has many groups —$N(R^3)H$ but Formula (I) shows only one for ease of discussion purposes only. The —$N(R^3)H$ groups can be a primary or secondary amino group and can be part of a pendant group or part of the backbone of the precursor polymer. The amino-containing polymers can be synthesized or can be naturally occurring biopolymers. Suitable amino-containing polymers can be prepared by chain growth or step growth polymerization procedures with amino-containing monomers. These monomers can also, if desired, be copolymerized with other monomers without an amino-containing group. Additionally, the amino-containing polymers can be obtained by grafting primary or secondary amine groups using an appropriate grafting technique.

The guanidinyl-containing polymer also includes polymers where the guanidinyl moiety is protonated including polymers having the following formula:

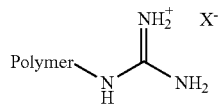

with $X^-$ being selected from $Cl^-$, $Br^-$, $I^-$, $½ SO_4^{2-}$, $NO_3^-$, $CH_3COO^-$, $C_3H_7COO^-$.

Examples of amino-containing polymers suitable for use, which can be prepared by chain growth polymerization include, but are not limited to, polyvinylamine, poly(N-methylvinylamine), polyallylamine, polyallylmethylamine, polydiallylamine, poly(4-aminomethylstyrene), poly(4-aminostyrene), poly(acrylamide-co-methylaminopropylacrylamide), and poly(acrylamide-co-aminoethylmethacrylate).

Examples of amino-containing polymers suitable for use, which can be prepared by step growth polymerization include, but are not limited to, polyethylenimine, polypropylenimine, polylysine, polyaminoamides, polydimethylamine-epichlorohydrin-ethylenediamine, and any of a number of polyaminosiloxanes, which can be prepared from monomers such as aminopropyltriethoxysilane, N-(2-aminoethyl)-3-aminopropyltrimethoxysilane, N-trimethoxysilylpropyl-N-methylamine, and bis(trimethoxysilylpropyl)amine.

Other useful amino-containing polymers that have primary or secondary amino end groups include, but are not limited to, dendrimers (hyperbranched polymers) formed from polyamidoamine (PAMAM) and polypropylenimine. Exemplary dendrimeric materials formed from PAMAM are commercially available under the trade designation "STARBURST (PAMAM) dendrimer" (e.g., Generation 0 with 4 primary amino groups, Generation 1 with 8 primary amino groups, Generation 2 with 16 primary amino groups, Generation 3 with 32 primary amino groups, and Generation 4 with 64 primary amino groups) from Aldrich Chemical (Milwaukee, Wis.). Dendrimeric materials formed from polypropylenimine are commercially available under the trade designation "DAB-Am" from Aldrich Chemical. For example, DAB-Am-4 is a generation 1 polypropylenimine tetraamine dendrimer with 4 primary amino groups, DAB-Am-8 is a generation 2 polypropylenimine octaamine dendrimer with 8 primary amino groups, DAB-Am-16 is a generation 3 polypropylenimine hexadecaamine with 16 primary amino groups, DAB-Am-32 is a generation 4 polypropylenimine dotriacontaamine dendrimer with 32 primary amino groups, and DAB-Am-64 is a generation 5 polypropylenimine tetrahexacontaamine dendrimer with 64 primary amino groups.

Examples of suitable amino-containing polymers that are biopolymers include chitosan as well as starch that is grafted with reagents such as methylaminoethylchloride.

Still other examples of amino-containing polymers include polyacrylamide homo- or copolymers and amino-containing polyacrylate homo- or copolymers prepared with a monomer composition containing an amino-containing monomer such as an aminoalkyl(meth)acrylate, (meth)acrylamidoalkylamine, and diallylamine.

For some embodiments, the preferred amino-containing polymers include polyaminoamides, polyethyleneimine, polyvinylamine, polyallylamine, and polydiallylamine.

Suitable commercially available amino-containing polymers include, but are not limited to, polyamidoamines that are available under the trade designations ANQUAMINE (e.g., ANQUAMINE 360, 401, 419, 456, and 701) from Air Products and Chemicals (Allentown, Pa.), polyethylenimine polymers that are available under the trade designation LUPASOL (e.g., LUPASOL FG, PR 8515, Waterfree, P, and PS) from BASF Corporation (Resselaer, N.Y.), polyethylenimine polymers such as those available under the trade designation CORCAT P-600 from EIT Company (Lake Wylie, S.C.), and polyamide resins such as those available from Cognis Corporation (Cincinnati, Ohio) under the traded designation VERSAMID series of resins that are formed by reacting a dimerized unsaturated fatty acid with alkylene polyamines.

Guanidinyl-containing polymers can be prepared by reaction of an amino-containing polymer precursor with a guanylating agent.

Although all the amino groups of the amino-containing polymer can be reacted with the guanylating agent, there are often some unreacted amino groups from the amino-containing polymer precursor remaining in the guanidinyl-containing polymer. Typically, at least 0.1 mole percent, at least 0.5 mole percent, at least 1 mole percent, at least 2 mole percent, at least 10 mole percent, at least 20 mole percent, or at least 50 mole percent of the amino groups in the amino-containing polymer precursor are reacted with the guanylating agent. Up to 100 mole percent, up to 90 mole percent, up to 80 mole percent, or up to 60 mole percent of the amino groups can be reacted with the guanylating agent. For example, the guanylating agent can be used in amounts sufficient to functionalize 0.1 to 100 mole percent, 0.5 to 90 mole percent, 1 to 90 mole percent, 1 to 80 mole percent, 1 to 60 mole percent, 2 to 50 mole percent, 2 to 25 mole percent, or 2 to 10 mole percent of the amino groups in the amino-containing polymer.

Known guanylating agents for reaction with an amino-containing polymer precursor include, but are not limited to, cyanamide; O-alkylisourea salts such as O-methylisourea sulfate, O-methylisourea hydrogen sulfate, O-methylisoura acetate, O-ethylisourea hydrogen sulfate, and O-ethylisourea hydrochloride; chloroformamidine hydrochloride; 1-amidino-1,2,4-triazole hydrochloride; 3,5-dimethylpyrazole-1-carboxamidine nitrate; pyrazole-1-carboxamidine hydrochloride; N-amidinopyrazole-1-carboxamidine hydrochloride; and carbodiimides such as dicyclohexylcarbodiimide, N-ethyl-N'-(3-dimethylaminopropyl)carbodiimide, and diisopropylcarbodiimide. The amino-containing polymer may also be acylated with guanidino-functional carboxylic acids such as guanidinoacetic acid and 4-guanidinobutyric acid in the presence of activating agents such as EDC (N-[3-(dimethylamino)propyl]-3-ethylcarbodiimide hydrochloride), or EEDQ (2-ethoxy-1-ethoxycarbonyl-1,2-dihydroquinoline). Additionally, the guanidinyl-containing polymer may be prepared by alkylation with chloroacetone guanyl hydrazone, as described in U.S. Pat. No. 5,712,027 (Ali et al.).

Guanylating agents for the preparation of biguanide-containing polymers include sodium dicyanamide, dicyanodiamide and substituted cyanoguanidines such as $N^3$-p-chlorophenyl-N1-cyanoguanidine, $N^3$-phenyl-$N_1$-cyanoguanidine, $N^3$-alpha-naphthyl-$N^1$-cyanoguanidine, $N^3$-methyl-N1-cyanoguanidine, $N^3,N^3$-dimethyl-$N^1$-cyanoguanidine, $N^3$-(2-hydroxyethyl)-$N^1$-cyanoguanidine, and $N^3$-butyl-$N^1$-cyanoguanidine. Alkylene- and arylenebiscyanoguanidines may be utilized to prepare biguanide functional polymers by chain extension reactions. The preparation of cyanoguanidines and biscyanoguanidines is described in detail in Rose, F. L. and Swain, G. J. Chem Soc., 1956. pp. 4422-4425. Other useful guanylating reagents are described by Alan R. Katritzky et al., Comprehensive Organic Functional Group Transformation, Vol. 6, p. 640.

The guanidinyl-containing polymer, in particular the polymer formed by reaction of an amino-containing polymer precursor and a guanylating agent will have pendent or catenary guanidinyl groups of the Formula (III).

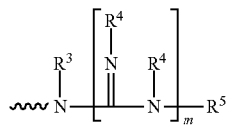

(III)

In Formula (III), m is equal to 1 or 2 and the groups $R^3$, $R^4$, and $R^5$ are the same as defined above. The wavy line attached to the $N(R^3)$ group shows the position of attachment the group to the rest of the polymeric material. In most embodiments, the group of Formula (III) is in a pendant group of the guanidinyl-containing polymer.

In some embodiments, it may be advantageous to react the amino-containing polymer precursor to provide other ligands or groups in addition to the guanidinyl-containing group. For example, it may be useful to include a hydrophobic ligand, an ionic ligand, or a hydrogen bonding ligand. This can be particularly advantageous for the removal of certain microorganisms during the wiping of a microorganism-contaminated surface.

The additional ligands can be readily incorporated into the amino-containing polymers by alkylation or acylation procedures well known in the art. For example amino groups of the amino-containing polymer can be reacted using halide, sulfonate, and sulfate displacement reactions or using epoxide ring opening reactions. Useful alkylating agents for these reactions include, for example, dimethylsulfate, butyl bromide, butyl chloride, benzyl bromide, dodecyl bromide, 2-chloroethanol, bromoacetic acid, 2-chloroethyltrimethylammonium chloride, styrene oxide, glycidyl hexadecyl ether, glycidyltrimethylammonium chloride, and glycidyl phenyl ether. Useful acylating agents include, for example, acid chlorides and anhydrides such as benzoyl chloride, acetic anhydride, succinic anhydride, and decanoyl chloride, and isocyanates such as trimethylsilylisocyanate, phenyl isocyanate, butyl isocyanate, and butyl isothiocyanate. In such embodiments 0.1 to 20 mole percent, preferably 2 to 10 mole percent, of the available amino groups of the amino-containing polymer may be alkylated and/or acylated.

The guanidinyl-containing polymer can be crosslinked. The amino-containing polymer can be crosslinked prior to reaction with the guanylating agent. Alternatively, the guanidinyl-containing polymer can be crosslinked by reaction of a crosslinker with remaining amino groups from the amino-containing polymer precursor or with some of the guanidinyl groups. Suitable crosslinkers include amine-reactive compounds such as bis- and polyaldehydes such as glutaraldehyde, bis- and polygylcidylethers such as butanedioldiglycidylether and ethyleneglycoldiglycidylether, polycarboxylic acids and their derivatives (e.g., acid chlorides), polyisocyanates, formaldehyde-based crosslinkers such as hydroxymethyl and alkoxymethyl functional crosslinkers, such as those derived from urea or melamine, and amine-reactive silanes, such as 3-glycidoxypropyltrimethoxysilane, 3-glycidoxypropyltriethoxysilane, 5,6-epoxyhexyltriethoxysilane, (p-chloromethyl)phenyltrimethoxysilane, chloromethyltriethoxysilane, 3-isocyanatopropyltriethoxysilane, and 3-thiocyanatopropyltriethoxysilane.

In other embodiments, the guanidinyl-containing polymer is of Formula (IV), which corresponds to Formula (I) where n is equal to 1.

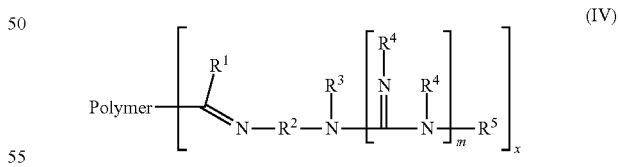

(IV)

In Formula (IV), the group $R^1$ is hydrogen, $C_1$-$C_{12}$ (hetero)alkyl, or $C_5$-$C_{12}$ (hetero)aryl, or a residue of the polymer chain. If the guanidinyl-containing group is the reaction product of a guanylating agent and a carbonyl group that is part of the backbone of the polymer, $R^1$ is a residue of the polymer chain. Group $R^2$ is a covalent bond, a $C_2$-$C_{12}$ (hetero)alkylene, or a $C_5$-$C_{12}$ (hetero)arylene. Group $R^3$ is hydrogen, $C_1$-$C_{12}$ (hetero)alkyl, or $C_5$-$C_{12}$ (hetero)aryl. Each $R^4$ is independently H, $C_1$-$C_{12}$ (hetero)alkyl, or $C_5$-$C_{12}$ (hetero)aryl. Group $R^5$ is hydrogen, $C_1$-$C_{12}$ (hetero)alkyl, or $C_5$-$C_{12}$ (hetero)aryl, or —$N(R^4)_2$. The variable m is equal to 1 or 2. The term "Polymer" in Formula (I) refers to all portions of the guanidinyl-containing polymer except the x groups of formula —C(R$^1$)=N—R$^2$—N(R$^3$)—[C(=NR$^4$)—NR$^4$R$^5$—]$_m$. The term x is a variable equal to at least 1.

Guanidinyl-containing polymers of Formula (IV) are the reaction product of a carbonyl-containing polymer and a suitable guanylating agent for reaction with a carbonyl group. The carbonyl-containing polymer used as a precursor polymer to prepare a guanidinyl-containing polymer of Formula (IV) can be represented by the formula Polymer —C(O)—R$^1$. The carbonyl-containing polymer precursor typically has many groups —C(O)—R$^1$ but Formula (IV) shows only one for ease of discussion purposes only. The carbonyl group —C(O)—R$^1$ is an aldehyde group (when R$^1$ is hydrogen) or a ketone groups (when R1 is a (hetero)alkyl or (hetero)aryl). Although the carbonyl-group can be part of the polymeric backbone or part of a pendant group from the polymeric backbone, it is typically in a pendant group.

If desired, the guanidinyl-containing polymers can be produced as described in US 2016/0115430 A1 (Swanson et al.), in particular, in sections [0049] to [0080], the description of which is herewith incorporated by reference.

The guanidinyl-containing polymer is typically present in the following amounts:
Lower limit: at least 1 or at least 2 or at least 5 wt. %;
Upper limit: utmost or utmost 40 or utmost 30 wt. %;
Range: from 1 to 60 or from 2 to 40 or from 5 to 30 wt. %;
wt. % with respect to the total amount of the dental retraction composition.

According to one embodiment, the dental retraction composition described in the present text comprises in addition polycresulen(s).

In the literature policresulen is described as being a hemostatic and antiseptic pharmaceutical drug.

Polycresulen can be described by Formula (V):

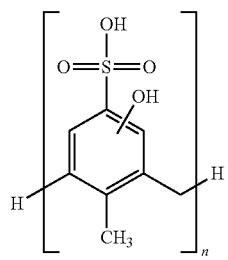

with n=from 2 to 50 or 2 to 20 or from 2 to 10.

It was found that adding polycresulen may help to reduce the force needed to extrude the dental retraction composition described in the present text from a packaging material.
If present, polycresulen(s) are typically present in the following amounts:
Lower limit: at least 0.1 or at least 1 or at least 2 wt. %;
Upper limit: utmost 20 or utmost 15 or utmost 10 wt. %;
Range: from 0.1 to 20 or from 1 to 15 or from 2 to 10 wt. %;
wt. % with respect to the total amount of the dental retraction composition.

The dental retraction composition described in the present text may further comprise one or more additive(s).

Additives, which can be present in the composition, include colourant(s), pharmaceutical drug(s), anti-microbial agent(s), flavouring agent(s), preserving agent(s), surfactant(s), antioxidant(s), rheology modifiers and mixtures and combinations thereof.

There is no need for additives to be present, however, if one or more additives are present, they are typically present in an amount which supports the intended purpose, that is, to facilitate the whole retraction procedure.

According to one embodiment, the dental retraction composition has a colour which may allow an easy detection in a patient's mouth (especially compared to oral tissue and/or tooth substance) and control whether after the treatment all residues of the retraction device have been removed from the sulcus. E.g., a blue, green or yellow colour may be suitable. However, in view of some new impression techniques like e.g. digital scanning, other colours might be preferred. Some techniques prefer colours that are less visible for the scanning instrument e.g. red or white. Colouring of the retraction device can be achieved by incorporating colorants or pigments (organic and inorganic) into the composition.

Examples of colourants which can be used include chinoline yellow dye (sicovit), chromophtalblue A3R, red iron oxide 3395, Bavferrox 920 Z Yellow, Neazopon Blue 807 (copper phthalocyanine-based dye), Helio Fast Yellow ER, Brilliant Blue FCF, Fast Green FCF and/or Orange Yellow S. Pigments or dyes which are stable under acidic conditions are preferred.

According to a further embodiment, rheology modifiers can be added. Rheology modifiers might contribute to the viscosity and effect the rinsability. Rheology modifiers which can be added include silicone oil. According to a further embodiment, pharmaceutical drugs can be added.

Pharmaceutical drugs might contribute or enhance a haemostatic effect, e.g. caused by the addition of an astringent. Pharmaceutical drugs which can be added include adrenaline, epinephrine, norepinephrine, noradrenalin, teryzolin, oxymetazolin propylhexidrin, adrenochrom-monosemicarbazone and other beta-2 sympathomimetika, propylgallat, tranexamic acid, etamsylate, batroxobin, thrombin, fibrin.

In another embodiment of the invention, the dental retraction composition may comprise one or more surfactants.

Typical surfactants, which can be used, include anionic, cationic or non-ionic surfactants.

There is no need for a surfactant to be present at all. However, if a surfactant is present, it is typically present in an amount of up to 2 wt. % or up to 1 wt. % or up to 0.05 wt. %, with respect to the whole composition.

In another embodiment of the invention, the dental retraction composition may comprise a flavouring agent(s) to improve the taste and/or smell of the composition.

Typical flavouring agent(s), which can be used, include but are not limited to Isoamylacetate (banana), Benzaldehyde (bitter almond). Cinnamic aldehyde (Cinnamon), Ethylpropionate (fruity), Methyl anthranilate (Grape), mints (e.g. peppermints), Limonene (e.g. Orange), Allylhexanoate (pineapple), Ethylmaltol (candy), Ethylvanillin (Vanilla), Methylsalicylate (Wintergreen).

There is no need for a flavouring agent to be present at all. However, if a flavouring agent is present, it is typically present in an amount of up to 3 wt. % or up to 0.1 wt. % of up to 0.01 wt. %, with respect to the whole composition.

If present, the additive(s) are typically present in the following amounts:
Lower limit: at least 0.01 or at least 0.1 or at least 0.5 wt. %;
Upper limit: utmost 20 or utmost 15 or utmost 10 wt. %;

Range: from 0.01 to 20 or from 0.1 to 15 or from 0.5 to 10 wt. %;

wt. % with respect to the total amount of the dental retraction composition.

A process of manufacturing the dental retraction composition described in the present text typically comprises the steps of providing the individual components to be mixed and mixing the components.

The dental retraction composition as described in the present text is typically contained in a container.

The dental retraction composition is preferably provided to the practitioner under hygienic conditions. One possibility to achieve this includes packing or storing the dental retraction composition in a sealed container such as a capsules, cartridge or foil bag under hygienic conditions.

Thus, the dental retraction composition is typically stored in a container or storage device. Usually, the container has a front end and a rear end, a piston movable in the container and a nozzle or cannula for delivering or dispensing the composition located in the container. The container has usually only one compartment or reservoir.

The container typically has a volume in the range from 0.1 to 1 ml. This is the volume typically needed for a single dental retraction procedure. The container is typically used only once (e.g. disposable packing).

The dental retraction composition can be dispensed out of the container by moving the piston in the direction of the nozzle. The piston can be moved either manually or with the aid of an application device or applier designed to receive the container (e.g. an application device having the design of a caulk gun).

Examples of containers which can be used include compules, syringes and screw tubes. Containers of this kind are exemplified in more detail e.g. in U.S. Pat. No. 5,927,562 (Hammen et al.), U.S. Pat. No. 5,893,714 (Arnold et al.) or U.S. Pat. No. 5,865,803 (Major).

It can be advantageous, if a container is used comprising a nozzle having a shape and size, which allows an easy and safe application of the dental retraction composition in the sulcus.

Useful containers typically have a hollow body (typically of cylindrical or conical shape) with a front end and a rear end in which the dental retraction composition is stored. The rear end is typically sealed with a piston, being movable in the hollow body. At the front end of the hollow body, there is typically a nozzle having a size and shape which enables the practitioner to dispense the inventive dental retraction composition into the sulcus of a patient. The smaller the diameter of the nozzle is, the easier the nozzle can be placed into the sulcus. However, a small diameter of the nozzle may result in an increase of the extrusion force needed to dispense the dental retraction composition out of the device. Thus, not all cannula sizes and diameters are suitable. A device with a nozzle or cannula having an external diameter in the range from 0.6 mm to 1.3 mm and an internal diameter in the range from 0.2 mm to 0.9 mm has been found to be particular useful.

However, other shapes and diameters can be used as well, if the intended effect (i.e. widening of the sulcus) can be achieved.

It has been found that especially a certain container containing the dental retraction composition described in the present text is particularly suited to address one or more objects of the invention. Such a container is described in more detail in US 2011/151403 A (Pauser et al.).

The container which can advantageously be used for storing and dispensing the dental retraction composition comprises a cannula that has a free end which comprises an opening for dispensing the dental composition.

Such a container facilitates the application of the composition into the sulcus in that it provides a mechanical means which allows an easy widening of the sulcus with the aid of the cannula. Once the sulcus has been widened, the composition can easily be applied and due to its sufficient flow resistance may help stabilizing the widened sulcus.

In one embodiment the free end and the opening are shaped so that the opening can be positioned to the entry of the gingival sulcus, with an outer lateral surface of the free end touching the tooth and the gingiva. The free end is further preferably shaped so that the gingiva is laterally displaced, for example predominantly laterally displaced, from the tooth as the cannula is further moved with the opening toward the inside of the gingival sulcus. Thus, the cannula preferably allows for injecting the dental retraction composition in a pre-opened gingival sulcus which may help to reliably fill the gingival sulcus with the dental retraction composition.

In another embodiment the free end has an outer lateral surface which extends between a first outer diameter D1 and a second outer diameter D2. Preferably the first outer diameter D1 is located adjacent the front of the free end, or at the front most end. The second outer diameter D2 is preferably located at a distance L2 further to the rear from the first outer diameter D1. D2 is preferably greater than D1. This preferably enables the device to displace the gingiva laterally away from the tooth, and preferably thereby enables the device to widen the gingival sulcus as the free end is moved farther into the gingival sulcus. The term "diameter" may be generally interpreted as "cross-sectional dimension", for cases in which a non-circular cross-section is provided.

The diameter D1 may be between 0.2 mm and 1 mm, in particular between 0.3 mm and 0.7 mm, or between 0.3 mm and 0.8 mm, in more particular D1 may be within a range of 0.4 mm to 0.6 mm. The diameter D1 is preferably about 0.4 mm. A relatively small dimension of the outer diameter D1 preferably allows, for example, the front of the free end to be inserted in the entry of the gingival sulcus relatively easily. Further such dimensions may help to reduce the risk of injuries of the gingival tissue during insertion of the front of the free end in the entry of the gingival sulcus, because it fits between the tooth and the gingiva rather than pressing on the gingiva itself.

The diameter D2 may be between 0.7 mm and 1.4 mm, in particular between 0.7 mm and 1.3 mm, in more particular the diameter D2 may be between 0.9 and 1.3 mm. Preferably the diameter D2 is about 1.1 mm more preferably 1.0 mm. Such dimensions may for example provide the free end of the cannula with a sufficient stiffness, and on the other hand may still provide good interproximal access for the free end. Therefore, the device described in the present text may be suitable to inject a dental retraction composition in the gingival sulcus all around a tooth in a controlled manner, and not only at distal or lingual portions of the gingival sulcus.

The length L2 of the free end may be between 0.3 mm and 2 mm, in particular between 0.3 mm and 1 mm, and preferably about 0.5 mm.

In another embodiment the first outer diameter D1 is located adjacent the opening. The first outer diameter D1 may also be formed by the opening. The opening may have a first inner diameter P1 which is between 0.2 mm and 1 mm, however the opening may further have a first inner diameter P1 which is between 0.3 mm and 0.7 mm. In particular P1 may be within a range of 0.4 mm to 0.6 mm, and preferably about 0.4 mm. P1 may be smaller than D1, but is preferably about equal to D1. In latter case P1 and D1 both refer to the diameter of the opening. In particular, the inner diameter P1 may provide for the flow rate of a high viscosity dental composition to be controlled relatively precisely as the composition is injected into the gingival sulcus.

In another embodiment the lateral outer surface of the free end tapers from the second outer diameter D2 toward the first outer diameter D1. Thus, the taper preferably tapers in a direction from D2 toward D1. Furthermore the taper preferably tapers based on a curve having a relatively constant radius R. The Radius R may be greater than ½ of D2. For example, the shape of the free end may resemble a nose cone, a convex cone, or a radial cone. A curve resembling a radius greater than ½ of D2 may provide for a relatively low force required to insert the free end of the cannula in the entry of the gingival sulcus. Relative to a linear cone such convex or radial cone may further provide for a less blunt front-most end, which may reduce the risk of injuring the gingiva when inserted into the gingival sulcus.

The cannula of the container may have a length L1 between the first outer diameter D1 and a third outer diameter D3. The cannula may have a shaft portion extending between the second outer diameter D2 and the third outer diameter D3. The shaft portion and the free end may be located adjacent to each other, and together extend along the length L1. The third outer diameter D3 may be between 0.7 mm and 2 mm, in particular between 1.3 mm to 1.9 mm, and preferably about 1.7 mm. D3 is preferably greater than D2, but may also be about equal to D2. Thus, the shaft portion may be generally cylindrical or conical. Preferably the shaft portion smoothly transitions to the free end. The length L1 may be between 6 mm and 18 mm, in particular between 8 mm and 10 mm, and preferably about 9 mm. Such dimensions preferably allow the cannula to access areas that are accessible only through narrow spaces in a patient's mouth, for example a gingival sulcus between two teeth. This may also help in injecting a dental composition around substantially the entire perimeter of a tooth.

In one embodiment the cannula has a marking. The marking preferably is usable as reference with regard to a certain (for example a preferred) penetration depth of the cannula in the gingival sulcus. The marking may help a user to observe and/or to assess the depth to which the cannula is inserted in the gingival sulcus during a treatment of a patient. Therefore, a user may control the penetration depth of the cannula relatively precisely and thereby may achieve an effective gingival retraction. On the other hand this may help to avoid damage to the gingival tissue which may result from too deep penetration of the cannula in the gingival sulcus. The marking may be a notch, a rim, a step, or a (printed) line, for example. The marking may extend partly or entirely circumferentially around the cannula. The marking may further be formed by a transition between colors of outside surfaces of the cannula. For example, the front end of the cannula may have a certain first outside color, and an adjacent rear portion of the cannula may have a certain second outside color, wherein the first and second colors are different. The marking may also be formed by a transition between areas of different transparency or translucency. Preferably the marking is formed by a transition between surface structures of outside surfaces of the cannula. For example, the front end of the cannula may have a generally even or glossy outside surface, and an adjacent rear portion of the cannula may have a more rough or matt outside surface. The marking may also be a scale marking different penetration depths.

In one embodiment the container comprises a cartridge having a chamber for receiving and storing the dental retraction composition. The container is preferably adapted for comprising a piston, or may comprise a piston. The container is preferably adapted for dispensing the dental retraction composition through the cannula. The cartridge may extend along a longitudinal axis, and the piston may be movable along the longitudinal axis for urging the dental retraction composition towards the cannula. The chamber may, for example open into a nozzle to which the cannula can be adapted. Alternatively the chamber may open into the cannula. The cannula may be fixedly attached to the cartridge. For example, the cannula and the cartridge may be co-injection molded. In another embodiment the cannula and the cartridge are made from different plastic materials. For example the cartridge may be made of a more rigid plastic material than the cannula. Therefore, the cartridge may provide sufficient stability for extruding the composition, and the cannula may be sufficiently soft to reduce the risk of injuries of the gingiva while in use.

In another embodiment the cannula may extend along a longitudinal axis which is inclined relative to the longitudinal axis of the cartridge by an angle of between 30 degrees and 60 degrees, preferably by about 45 degrees. The cannula may also extend along a curve, and a central axis through the opening of the cannula may be inclined relative to the longitudinal axis of the cartridge by an angle of between 30 degrees and 60 degrees, preferably by about 45 degrees.

In another embodiment the cannula comprises a passageway between the opening with the first inner diameter P1 and an inlet with a second inner diameter P2, wherein P2 is between 0.3 and 1.0 mm. P2 is preferably greater than or equal to P1. Thus the passageway may taper towards the opening which may in dispensing certain dental compositions provide for a reduced extrusion force. Alternatively the passageway may be generally cylindrical which may facilitate manufacturing.

In another embodiment the convexly tapered outer surface of the free end may meet with the inner surface of the passageway at an angle of less than 90 degrees. It has been found that an angle below 90 degrees between the outer surface of the free end and the inner surface of the passageway may provide for a relatively low force required to insert the front of the free end into the entry of the gingival sulcus.

Materials which can be used for producing the cannula include polyethylene, polypropylene, styrene-butadiene-styrene block copolymer, styrene-butadiene-methacrylate block copolymer, and thermoplastic polyurethane. Preferred plastic material for the container include polyamide, polyoxymethylene, polypropylene and polycarbonate.

Described is also a kit of parts comprising part A and part B, part A comprising the dental retraction composition as described in the present text and part B comprising one or more of the following components: applier, dental impression material, retraction caps and/or instruction for use.

Thus, the kit of parts may comprise besides a dental retraction composition as described in the present text a dental impression material.

The dental impression materials which can be used in combination with retraction devices are not particularly limited in regard to their chemistry and nature. Polyether moieties or silicone moieties containing impression materials have found to be useful.

Examples of polyether moieties containing impression materials are given in U.S. Pat. No. 6,383,279 (Eckhardt et al.) and US 2002/0156149 (Schaub et al.). Commercially available materials are sold e.g. under the brand Impregum™ (3M Oral Care/3M ESPE).

Examples of silicone moieties containing impression materials are given in U.S. Pat. No. 8,563,625 (Zech et al.), US 2007/004858 (Zech et al.) and US 2006/293469 (Zech et al.). Commercially available materials are sold e.g. under the brand Imprint™ (3M Oral Care/3M ESPE). The kit may also comprise retraction caps.

Retraction caps can be useful for keeping the retraction material in place until an impression is taken or pushing the dental retraction composition into the sulcus. Retraction caps can be made of soft, tissue friendly material, e.g. cotton. However, other materials might be useful as well. If appropriate a temporary restoration can be used as retraction cap, too. Commercially available retraction caps are e.g. sold under the brand Comprecap™ (Coltène Whaledent).

In some cases compression caps or bridges, temporary crowns or bridges or even a first impression might be used as a kind of accessory during the retraction process.

Typically, the dental retraction composition remains in the sulcus for a couple of minutes (e.g. 1 to 10 or 2 to 6 min to achieve effective mechanical retraction. The kit may also comprise an applier or capsule dispenser.

Those devices are commercially available e.g. from 3M Oral Care, 3M ESPE (cf. Product Catalogue 2007, page 29). Typical appliers have a gear ratio from about 3:1 to about 4:1. A further example of an applier, which can be used, is shown in U.S. Pat. No. 5,362,495, FIG. 3.

Described is also a process of dispensing the dental retraction composition as described in the present text.

The process typically comprises the following steps:
providing a device or container containing the dental retraction composition as described in the present text,
placing the device or container in an applier or dispenser.
using the applier or dispenser to dispense the dental retraction composition.
These steps can be repeated, if desired.

A method of retracting soft tissue from hard dental tissue typically comprises the steps of:
dispensing the dental retraction composition as described in the present text into the sulcus between soft and hard dental tissue,
leaving or retaining the dental retraction composition in the sulcus e.g. for at least about 10 s or at least about 30 s or at least about 60 s,
removing the dental retraction composition from the sulcus and
optionally making an impression of the hard dental tissue.

Described is also the use of a dental retraction composition as described in the present text for producing a means for retracting soft tissue form hard dental tissue, the means typically comprising a container with a cannula and a reservoir, wherein the composition is stored in the reservoir before use.

According to one embodiment, the dental retraction composition is inserted into the sulcus by the aid of the front end of the cannula of the container. This may facilitate the mechanically opening of the sulcus between soft and hard dental tissue.

A typical application procedure can be exemplified as follows:

The dental retraction composition is dispensed by means of an applier out of a nozzle or cannula of a container into the sulcus of a prepared tooth structure of a mammal or human being. The dental retraction composition remains in the sulcus for an appropriate time period, which is typically determined by the practitioner.

After sufficient retraction, the composition is removed from the sulcus using e.g. a dental water air syringe having sufficient pressure. Water-air beam devices are typically included in a dental chair.

The sulcus has been widened due to the application of the dental retraction composition compared to the sulcus before the application. After removal of the dental retraction composition the shape of the prepared tooth including the preparation margin can be determined, either by an impression-taking process with a common impression material or by an intra-oral scan of the prepared region using e.g. an inter-oral scanner such as the True Definition Scanner (chairside oral scanner) provided by 3M/3M ESPE.

If desired the whole process and workability can also be demonstrated in vitro, e.g. using a Frasaco™ Standard Model AG3 (synthetic tissue surrounding an artificial tooth).

Further embodiments are described below:

Embodiment 1 relates to a dental retraction composition as described in the present text comprising:
filler(s): from 5 to 70 wt. %,
paste forming liquid(s): from 10 to 60 wt. %,
guanidinyl-containing polymer(s), preferably guanidinyl-containing polyethylenimine(s) or polypropylenimine(s): from 1 to 60 wt. %.

Embodiment 2 relates to a dental retraction composition as described in the present text comprising:
phyllosilicate(s): from 20 to 70 wt. %,
paste forming liquid(s): from 10 to 60 wt. %,
guanidinyl-containing polymer(s), preferably guanidinyl-containing polyethylenimine(s) or polypropylenimine(s): from 1 to 60 wt. %.

Embodiment 3 relates to a dental retraction composition as described in the present text composition comprising:
phyllosilicate(s) selected from kaolinite, mica minerals and mixtures thereof and being present in an amount from 20 to 50 wt. %,
paste forming liquid(s) selected from glycol, ethylene glycol, poly(ethylene glycol), propylene glycol, poly(propylene glycol), and mixtures thereof and being present in an amount from 10 to 60 wt. %,
guanidinyl-containing polymer(s): the polymer being a polyethylene imine and being present in an amount from 1 to 60 wt. %,
wt. % with respect to the weight of the whole composition.

Embodiment 4 relates to a dental retraction composition as described in the present text composition comprising:
phyllosilicate(s) selected from kaolinite, mica minerals and mixtures thereof and being present in an amount from 25 to 65 wt. %,
paste forming liquid(s) selected from glycol, ethylene glycol, poly(ethylene glycol), propylene glycol, poly(propylene glycol), and mixtures thereof and being present in an amount from 15 to 50 wt. %,
guanidinyl-containing polymer(s): the polymer being a polyethylene imine and being present in an amount from 1 to 60 wt. %,
the dental retraction composition not comprising
aluminium salts in an amount above 2 wt. %,
water in an amount above 2 wt. %,
wt. % with respect to the weight of the whole composition.

Embodiment 5 relates to a dental retraction composition as described in the present text composition comprising:
filler(s),
paste forming liquid(s) having a boiling point above 100° C., guanidinyl-containing polymer(s), selected from polymer(s) being characterized by the following formula:

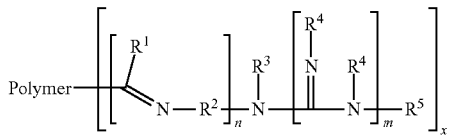

wherein:
$R^1$ is hydrogen, $C_1$-$C_{12}$ (hetero)alkyl, a $C_5$-$C_{12}$ (hetero) aryl, or a residue of the polymer chain,
$R^2$ is a covalent bond, a $C_2$ to $C_{12}$ (hetero)alkylene, or a $C_5$-$C_{12}$ (hetero)arylene;
$R^3$ is hydrogen, $C_1$-$C_{12}$ (hetero)alkyl, $C_5$-$C_{12}$ (hetero)aryl, or a residue of the polymer chain when n is 0;
each $R^4$ is independently hydrogen, $C_1$-$C_{12}$ (hetero)alkyl, $C_5$-$C_{12}$ (hetero)aryl;
$R^5$ is hydrogen, $C_1$-$C_{12}$ (hetero)alkyl, or $C_5$-$C_{12}$ (hetero) aryl, or —$N(R^4)_2$
n is 0 or 1;
m is 1 or 2; and
x is an integer equal to at least 1
and its protonated salts.

Embodiment 6 relates to a dental retraction composition as described in the present text composition comprising filler(s),
paste forming liquid(s) having a boiling point above 100° C.,
guanidinyl-containing polymer(s), selected from polymer(s) being characterized by the following formula:

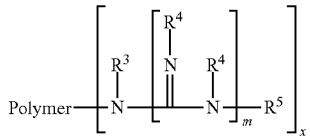

wherein:
$R^3$ is hydrogen,
each $R^4$ is independently selected from hydrogen, $C_1$-$C_{12}$ (hetero)alkyl, and $C_5$-$C_{12}$ (hetero)aryl, preferably hydrogen,
$R^5$ is selected from hydrogen, $C_1$-$C_{12}$ (hetero)alkyl, or $C_5$-$C_{12}$ (hetero)aryl, preferably hydrogen,
m is equal to 1 or 2,
x is a variable equal to at least 1,
and its protonated salts.

The dental retraction composition described in the present text does typically not contain components producing a toxic, injurious, or immunological response in living tissue or components or additives which jeopardize the intended purpose to be achieved with the present invention.

Thus, for examples components or additives added in an amount which finally result in a composition, the characteristics of which are in contradiction to the intended purpose of the invention, are usually not contained in the dental retraction composition.

According to a specific embodiment, the dental retraction composition does typically not contain one or more of the following components:
fibrillated fibres in an amount of more than 2 wt. %;
water absorbing agents like superabsorbers in an amount of more than 2 wt %;
water in an amount of more than 2 wt. %;
cross-linkable component(s) in an amount of more than 2 wt. %;
aluminium salts (like aluminium chloride, potassium or ammonium aluminium sulphate) in an amount of more than 2 wt. %.

Fibrillated fibres are e.g. natural fibres based on cellulose or man-made fibres e.g. polyester, polyamide or fibres of glass. It was found that the addition of fibres can sometimes be detrimental to the whole retraction process in that the fibre structure in the paste might decrease the flow resistance, compared to pastes without fibres.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof. The following examples are given to illustrate the invention.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Methods

Rinse Time

The rinse time was measured as follows: The pastes inserted into a 9 mm×1 mm×3 mm crevice in a plastic cone shaped block simulating a gingival sulcus, rinsed therefrom and the time required to clear it was measured. The floor of the crevice was positioned at a 45 degree angle to the line of the water stream. A dental air and water syringe delivered pressurized air at 2 bars and water at 1.8 bars simultaneously. The tip of the syringe was situated 5 mm from the crevice. The round plastic block underwent 60 rotations per minute.

The measurement of the rinse time is also as described in C. Decoteau, M. Ogledzki, S. Soroushian, R. D. Perry, Rinse Time of Hemostatic Retraction Pastes, IADR 2011 #1025.

Flow Resistance

The flow resistance was measured using a testing device Zwick Z020 machine (Zwick Roell Comp.). The testing device was equipped with a mould (diameter 8 mm, depth 5.6 mm) and a stamp (diameter 6 mm) to press the stamp against the paste inserted into the mould. The testing speed was set to 0.25 mm/s. The maximum force after 4 mm insertion was measured.

Extrusion Force

The extrusion force was measured using as testing device a Zwick Z020 machine (Zwick Roell Comp.). The testing device was equipped with a holder for containers and a small stamp to press against the piston inserted in the container and sealing the reservoir. The dimensions of the stamp corresponded to those used in commercially available single container dispensers (commercially available e.g. from 3M Oral Care, 3M ESPE; order code 5706 SD). The feeding speed was set to 1.0 mm/s. The force was measured after the initial yield point was overcome (about 6-9 mm from starting point). The extrusion force was determined as an average value out of six individual measurements.

Shelf-Life Time Experiments

The materials were stored in the capsules used for storing the commercially available product 3M ESPE Astringent Retraction Paste (retraction capsule). The retraction capsules were stored at room temperature and 50% rel. humidity without sealed pouches. The measurements were done at the start and after one week storage time and the results obtained are summarized in Table 2.

Residual Gap/Consistency

If desired, the residual gap can be determined as follows (cf. PCT/US16/33303, FIG. 1 and description on page 30): The capability of a composition to open a sulcus and to keep a sulcus open can be determined by a device using a stamp which creates pressure created by a spring onto the curable paste in a small slit (residual gap device).

More precisely, the method can be described as follows:

A mold having a rectangular shape with the dimensions: x (depth)=7.5 mm, y (width)=18.0 mm and z (height)=12.0 mm is provided.

The mold is formed by three immovable sidewalls and one movable sidewall, all located on a plane surface. The movable sidewall is equipped with a spring having a defined spring pressure of 20N. The spring is compressed and fixed by a removable fixation means. The moveable sidewall is adjusted to a pre-defined depth of 7.5 mm (x-direction). The mold is filled with the composition.

After a pre-defined time T1 (e.g. 60 sec), the fixation means of the spring is removed having the result that the spring exerts a predefined pressure on the composition through the movable sidewall. A portion of the composition is pressed out of the mold. The depth of the mold is decreasing which can be determined by measuring the distance for x (mm) using e.g. a length gauge.

After a pre-defined time T2 (e.g. 70 sec), the value for x (mm) is determined.

The higher the value x at time T2 is, the higher the consistency/residual gap behavior of the composition is.

Materials

TABLE 1

| Component | Description |
| --- | --- |
| Polyethyleneglycol dimethyl ether 400 | Paste forming liquid |
| Polydimethylsiloxane 3 mPa*s | Additive |
| g-PEI | Guanidinylated polyethyleneimine |
| Mica | Phyllosilicate (1:2) |
| Kaolinite | Phyllosilicate (1:1) |
| Irganox ™ 1010 | Antioxidant (sterically hindered phenol) |
| Policresulen | Astringent |
| Astringent Retraction Paste | Commercially available product (3M) for retraction purposes containing aluminium chloride, water, polydimethylsiloxane and phyllosilicates |
| Retraction capsules | Capsules in which the commercially available 3M ESPE Astringent Retraction Paste are stored. |

Cross-Linked Guanylated Polyethylenimine (g-PEI)

A 12 L 3-neck split top resin flask was charged with 1250 g of aqueous polyethyleneimine solution (mw 75,000, 32.6% solids, BASF Lupasol PS) followed by 1279 g of D1 water (de-ionized water). The flask was equipped with an overhead stirrer. 291.6 g of O-Methylisourea hemisulfate was added and the mixture stirred overnight. An aliquot was taken from the viscous solution and checked by 1H NMR (CD3OD) to monitor for the consumption of O-methylisourea hemisulfate. The solution was then transferred to a polypropylene bottle rinsing with a little water followed by measuring percent solids (21.1% by Ohaus).

The solution was then treated with 3401 g of heptanes and the resultant biphasic mixture stirred for 5 minutes. 1,4-Butanediol diglycidyl ether (BUDGE, 91.5 g) was added and the mixture was stirred overnight (16 hours). Stirring was ceased and the heptane and D1 water were removed from the mixture with a vacuum filter stick (coarse porosity). The resulting gel was washed with isopropyl alcohol to draw off remaining heptane. 2176 g of isopropyl alcohol was added to the flask. The mixture was stirred vigorously for 10 minutes and then filtered using the filter stick. This procedure was repeated three more times. The resulting white solid was then collected using a Nutsche filter and dried in a vacuum oven at 100° C. to provide the g-PEI in the form of beads.

The dried beads were then jet milled using a 3000 rpm Model 100/20 jet miller. The dried beads were placed in a hopper then feed into an air stream tube. The air stream carried the beads to a splitter where the beads were pushed through two smaller tubes and eventually forced through a cone shaped nozzles (jets). The jets were positioned so the beads collided into each other, the impact reduces the particle size. After the collision, the air stream carried the bead particles to a classifier. The classifier, depending on its rotational speed allowed small particles to be collected while larger particles were returned to the air stream to be jet milled again. Generally, higher classifier speeds result in finer particle size. The jet milled g-PEI beads had an average particle size less than 20 μm.

Paste Preparation

The following components were mixed in a speedmixer under vacuum to obtain a homogenous paste. The pastes were filled in retraction capsules.

Example 1

| | |
| --- | --- |
| Polyethyleneglycol Dimethyl ether 400 | 36.0 wt. % |
| Polydimethylsiloxane 3 mPa*s | 2.3 wt. % |
| g-PEI | 10.0 wt. % |
| Mica | 48.7 wt. % |
| Kaolinite | 3.0 wt. % |

Example 2

| | |
| --- | --- |
| Polyethyleneglycol Dimethyl ether 400 | 36.46 wt. % |
| Polydimethylsiloxane 3 mPa*s | 2.30 wt. % |
| g-PEI | 9.99 wt. % |
| Mica | 48.15 wt. % |
| Kaolinite | 3.00 wt. % |
| Irganox ™ 1010 | 0.10 wt. % |

Example 3 (Combination of Policresulen and Guanylated Polyethyleneimine

| | |
| --- | --- |
| Polyethylene glycol Dimethyl ether 400 | 35.00 wt % |
| Policresulen | 5.00 wt. % |

-continued

| | |
|---|---|
| Polydimethylsiloxane 3 mPa*s | 2.30 wt. % |
| g-PEI | 10.00 wt. % |
| Mica | 44.70 wt. % |
| Kaolinite | 3.00 wt. % |

Comparative Example 1 (C.E. 1

Astringent Retraction Paste (3M ESPE, batch #604143)

Comparative Example 2 (Only Policresulen

| | |
|---|---|
| Policresulen | 24.4 wt. % |
| Polyethylene glycol Dimethyl ether 400 | 10.0 wt. % |
| Mica | 62.5 wt. % |
| Kaolinite | 3.1 wt. % |

TABLE 2

| | C. E. 1 Astringent Retraction Paste #604143 | | Example 1 | | Example 2 | | C. E. 2 | Example 3 |
|---|---|---|---|---|---|---|---|---|
| | Shelf Life Exp. | | | | | | | |
| | 0 | 1 week | 0 | 1 week | 0 | 1 week | 0 | 0 |
| Rinse Time [s] | 8 | 22 | 3 | 8 | 5 | 5 | 60 | 6.0 |
| Extrusion Force [N] | 100.6 | 131.7 | 57.7 | 54.5 | 50.7 | 61.6 | 126 | 44.8 |
| Flow Resistance [N] | 23.3 | 25.6 | 16.9 | 16.4 | 13.4 | 14.1 | 29.3 | 15 |

It was found that the compositions described in the present text comprising guanidinyl-containing polymer(s) showed an improved rinse time even if the compositions were stored for 1 week compared to compositions not comprising guanidinyl-containing polymer(s).

Further, the extrusion force and flow resistance could be improved, if compositions as described in the present text were used.

If a combination of guanidinyl-containing polymer and policresulen(s) was used, the extrusion force of the composition could be even further reduced.

In addition, the haemostatic capability might be enhanced by the combination of two hemostatic active substances.

What is claimed is:

1. A dental retraction composition comprising:
   phyllosilicate filler(s),
   paste forming liquid(s),
   guanidinyl-containing polymer(s) derived from one or more amino-containing polymer selected from a polyvinylamine, a poly(N-methylvinylamine), a polyallylamine, a polyallylmethylamine, a polydiallylamine, a poly(4-aminomethylstyrene), a poly(4-aminostyrene), a poly(acrylamide-co-methylaminopropylacrylamide), a poly(acrylamide-co-aminoethylmethacrylate), a polyethylenimine, a polypropylenimine, a polylysine, a polyaminoamide, polydimethylamine-epichlorohydrin-ethylenediamine, a polyaminosiloxane, a dendrimer formed from a polyamidoamine and a polypropylenimine, a polyacrylamide, and an amino-containing polyacrylate, wherein the dental composition is characterized by a flow resistance greater than or equal to 8N.

2. The dental retraction composition of claim 1, comprising the components in following amounts:
   filler(s): from 5 to 70 wt. %,
   paste forming liquid(s): from 10 to 60 wt. %,
   guanidinyl-containing polymer(s): from 1 to 60 wt. %.

3. The dental retraction composition of claim 1, further comprising filler(s) selected from silicates, silicas, aluminas, magnesias, titanias, inorganic salts, metallic oxides, glasses, plastic powder, micro- and nanocrystalline cellulose, starch and mixtures thereof.

4. The dental retraction composition of claim 1, the phyllosilicate filler(s) selected from layer type 1:1 silicates, layer type 1:2 silicates and mixtures thereof.

5. The dental retraction composition of claim 1, the paste forming liquid(s) being characterized by one or more of the following features:
   Molecular weight: utmost 10,000 g/mol;
   Boiling point: above 100° C.;
   Viscosity: up to 35 Pa*s at 23° C.

6. The dental retraction composition of claim 1, the paste forming liquid(s) being selected from mono-alcohol(s), glycol(s), alkyl glycol ether(s), block-copolymer(s) of ethylene glycol and propylene glycol, copolymer(s) of ethylene glycol and tetrahydrofuran, copolymer(s) of ethylene glycol, propylene glycol and tetrahydrofuran, alkoxylated glycerine, alkoxylated pentaerythritol and mixtures thereof.

7. The dental retraction composition of claim 1, the guanidinyl-containing polymer(s) being characterized by the following formula:

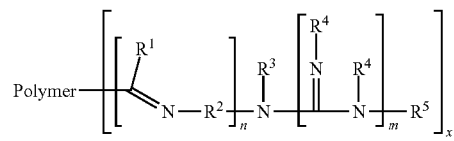

wherein:
$R^1$ is hydrogen, $C_1$-$C_{12}$ (hetero)alkyl, a $C_5$-$C_{12}$ (hetero)aryl, or a residue of the polymer chain;
$R^2$ is a covalent bond, a $C_2$ to $C_{12}$ (hetero)alkylene, or a $C_5$-$C_{12}$ (hetero)arylene;
$R^3$ is hydrogen, $C_1$-$C_{12}$ (hetero)alkyl, $C_5$-$C_{12}$ (hetero)aryl, or a residue of the polymer chain when n is 0;
each $R^4$ is independently hydrogen, $C_1$-$C_{12}$ (hetero)alkyl, $C_5$-$C_{12}$ (hetero)aryl;
$R^5$ is hydrogen, $C_1$-$C_{12}$ (hetero)alkyl, or $C_5$-$C_{12}$ (hetero)aryl, or $N(R^4)_2$;

n is 0 or 1;
m is 1 or 2; and
x is an integer equal to at least 1
and its protonated salts.

8. The dental retraction composition of claim 1, the guanidinyl-containing polymer(s) being selected from
Polymer(s) having pendent or catenary guanidinyl groups of the following formula:

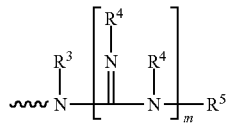

wherein, m is equal to 1 or 2 and the groups $R^3$, $R^4$, and $R^5$ are the same as defined above and its protonated salts,
or
Polymer(s) of the following formula:

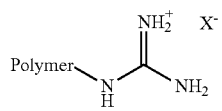

with $X^-$ being selected from $Cl^-$, $Br^-$, $I^-$, $½ SO_4^{2-}$, $NO_3^-$, $CH_3COO^-$, $C_3H_7COO^-$.

9. The dental retraction composition of claim 1, comprising:
filler(s) selected from phyllosilicate(s) and mixtures thereof and being present in an amount from 20 to 70 wt. %,
paste forming liquid(s) selected from glycol, ethylene glycol, poly(ethylene glycol), propylene glycol, poly (propylene glycol), copolymer(s) of ethylene glycol, propylene glycol and/or tetrahydrofuran and mixtures thereof and being present in an amount from 10 to 60 wt. %,
guanidinyl-containing polymer(s): the polymer being a polyethylene imine and being present in an amount from 1 to 60 wt. %,
the dental retraction composition not comprising either of the following alone or in combination
aluminium salts in an amount above 2 wt. %,
water in an amount above 2 wt. %,
wt. % with respect to the weight of the whole composition.

10. The dental retraction composition of claim 1, comprising in addition policresulen.

11. The dental retraction composition of claim 1, being contained in a delivery device, the delivery device having the shape of a capsule, compule, syringe, or cartridge.

12. The dental retraction composition of claim 1, for use in a process comprising the following steps:
providing the dental retraction composition of claim 1,
inserting the dental retraction composition into the sulcus of a tooth.

13. A kit of parts comprising:
a dental retraction composition comprising:
filler(s),
paste forming liquid(s), and
guanidinyl-containing polymer(s) derived from one or more amino-containing polymer selected from a polyvinylamine, a poly(N-methylvinylamine), a polyallylamine, a polyallylmethylamine, a polydiallylamine, a poly(4-aminomethylstyrene), a poly(4-aminostyrene), a poly(acrylamide-co-methylaminopropylacrylamide), a poly(acrylamide-co-aminoethylmethacrylate), a polyethylenimine, a polypropylenimine, a polylysine, a polyaminoamide, polydimethylamine-epichlorohydrin-ethylenediamine, a polyaminosiloxane, a dendrimer formed from a polyamidoamine and a polypropylenimine, a polyacrylamide, and an amino-containing polyacrylate; and
one or more of the following:
dental impression material(s);
applier(s);
retraction cap(s);
a set of instructions directing a user to:
dispense the dental retraction composition into a sulcus between the soft tissue and the hard dental tissue,
allowing the dental retraction composition to remain in the sulcus for a period, and
removing the dental retraction composition from the sulcus.

14. A method for retracting soft tissue from hard dental tissue, the method comprising:
dispensing a dental retraction composition into a sulcus between the soft tissue and the hard dental tissue,
the dental retraction composition comprising:
filler(s),
paste forming liquid(s), and
guanidinyl-containing polymer(s) derived from one or more amino-containing polymer selected from a polyvinylamine, a poly(N-methylvinylamine), a polyallylamine, a polyallylmethylamine, a polydiallylamine, a poly(4-aminomethylstyrene), a poly(4-aminostyrene), a poly(acrylamide-co-methylaminopropylacrylamide), a poly(acrylamide-co-aminoethylmethacrylate), a polyethylenimine, a polypropylenimine, a polylysine, a polyaminoamide, polydimethylamine-epichlorohydrin-ethylenediamine, a polyaminosiloxane, a dendrimer formed from a polyamidoamine and a polypropylenimine, a polyacrylamide, and an amino-containing polyacrylate;
allowing the dental retraction composition to remain in the sulcus for a period; and
removing the dental retraction composition from the sulcus.

* * * * *